United States Patent [19]
Morrey, Jr.

[11] Patent Number: 5,602,474
[45] Date of Patent: Feb. 11, 1997

[54] DETECTING CRACKS IN NON-UNIFORM AREAS OF METAL PARTS INCLUDING POSITION CORRELATION

[75] Inventor: Willard C. Morrey, Jr., Palm City, Fla.

[73] Assignee: United Technologies Corporation, Hartford, Conn.

[21] Appl. No.: 469,339

[22] Filed: Jun. 6, 1995

[51] Int. Cl.$^6$ .................... G01N 27/82; G01N 27/72; G01B 7/30
[52] U.S. Cl. .................. 324/238; 324/240; 364/551.02
[58] Field of Search ........................ 324/238, 228, 324/234, 239, 240, 225, 207.15, 207.16, 207.17, 207.22; 364/551.02, 571.01, 571.04, 571.05

[56] References Cited

U.S. PATENT DOCUMENTS

| | | |
|---|---|---|
| 4,383,218 | 5/1983 | Hansen et al. . |
| 4,445,088 | 4/1984 | Schübel . |
| 4,460,869 | 7/1984 | Buser et al. . |
| 4,556,846 | 12/1985 | D'Hondt . |
| 4,628,261 | 12/1986 | Hüschelrath . |
| 4,763,274 | 8/1988 | Junker et al. ................... 324/220 X |
| 4,821,204 | 4/1989 | Hüschelrath . |
| 4,843,320 | 6/1989 | Spies ........................... 324/240 |
| 5,130,651 | 7/1992 | Morrey, Jr. . |
| 5,140,264 | 8/1992 | Metala et al. .................. 324/219 |
| 5,371,462 | 12/1994 | Hedengren et al. ............ 324/232 X |

Primary Examiner—Sandra L. O'Shea
Assistant Examiner—Roger C. Phillips
Attorney, Agent, or Firm—Robert E. Greenstien

[57] ABSTRACT

Eddy current testing is performed at known locations on a metal object having recurring features to provide a data string that is applied to a signal processor that determines a template for one feature and conducts a correlation operation with the template and the data string to create a second string with peaks that periodically appear between two locations. The average width between those two locations is determined. The average value for each location in the second data string along the average distance between peaks is computed. The actual value of the second string at each location is combined with the average computed value to produce a deviation value that shows faults without a superimposed average geometry value. The location of the fault is indicated in response to the deviation signal.

4 Claims, 4 Drawing Sheets

DETECTING CRACKS IN NON-UNIFORM AREAS OF METAL PARTS INCLUDING POSITION CORRELATION

The invention was made under a U.S. Government contract, and the U.S. Government has rights herein.

TECHNICAL FIELD

This invention relates to techniques for detecting cracks and other flaws in metal parts, in particular, for distinguishing between cracks in non-uniform areas of the part.

BACKGROUND OF THE INVENTION

Eddy current testing is one way to test metal parts for cracks and other flaws. U.S. Pat. No. 5,130,651 discusses the use of eddy current probes for that purpose. Generally speaking, eddy current testing involves a process by which the metal part is exposed to a magnetic field, producing electric currents in the part. The path taken by these currents is disturbed by a flaw, altering the overall field in the area of the flaw. By comparing the field at different locations to a known field for a flawless area, the flaw can be identified.

In a gas turbine engine, compressor, turbine and fan blades are removably attached to alloy disks in so-called "broaches", which are specially machined slots along the outer edge of the disk that receive an identically profiled blade base. Cracks can be present in the curved regions in the broaches, but the eddy current patterns produced by the broaches can mask the crack when conventional eddy current testing techniques are used.

SUMMARY OF THE INVENTION

An object of the present invention to provide an eddy current testing technique that can identify flaws, such as cracks in those broaches.

According to the invention, peaks in an eddy current produced signal are used to generate an electronic template for one broach. The signal levels between peaks are correlated with signal levels at other locations producing other peaks. An average value for locations between an average width periodic signal (defined by the peaks) is computed. The average value is subtracted from the signal value for each discrete location between the peaks and the deviation indicates a flaw.

According to the invention, the perimeter of a compressor disk is mapped as discrete location increments from a starting point at one broach. The disk is rotated under an eddy current probe and the signal produced from the probe at each location is stored as a value specific to the location. An electronic template is created by finding two points that bracket a broach. The value for each point in the template is applied in a correlation function to the value for each location, a process that leads to identification of points at other locations corresponding to the same locations in the template. Periodic peak values are assumed to identify other broaches, and their respective locations are stored. The average width of a broach in location increments is determined from the width of the peaks. The average signal value for identical location increments between those periodic peaks is computed from the measured signal value for each location increment from a peak, producing an average value for the template. The average value is subtracted from the actual value for each increment point between the peaks. If the sum exceeds a stored value, a crack is present and a signal is produced along with the location associated with the signal. This subtracts off the average signal associated with geometry differences and leaves only deviation signals, which can be evaluated to determine if a crack is present. If so, a signal is produced, along with the location associated with the signal.

A feature of the invention is that the signals associated with varying geometry are subtracted out, leaving the raw flaw signals without the geometry signals superimposed on top, which normally makes it difficult to detect the flaw produced signals. Another feature is that the invention can be used to test other parts having recurring identical features.

Other objects, benefits and features of the invention will be apparent from the following discussion of the invention.

DETAILED DESCRIPTION

Figure 1:
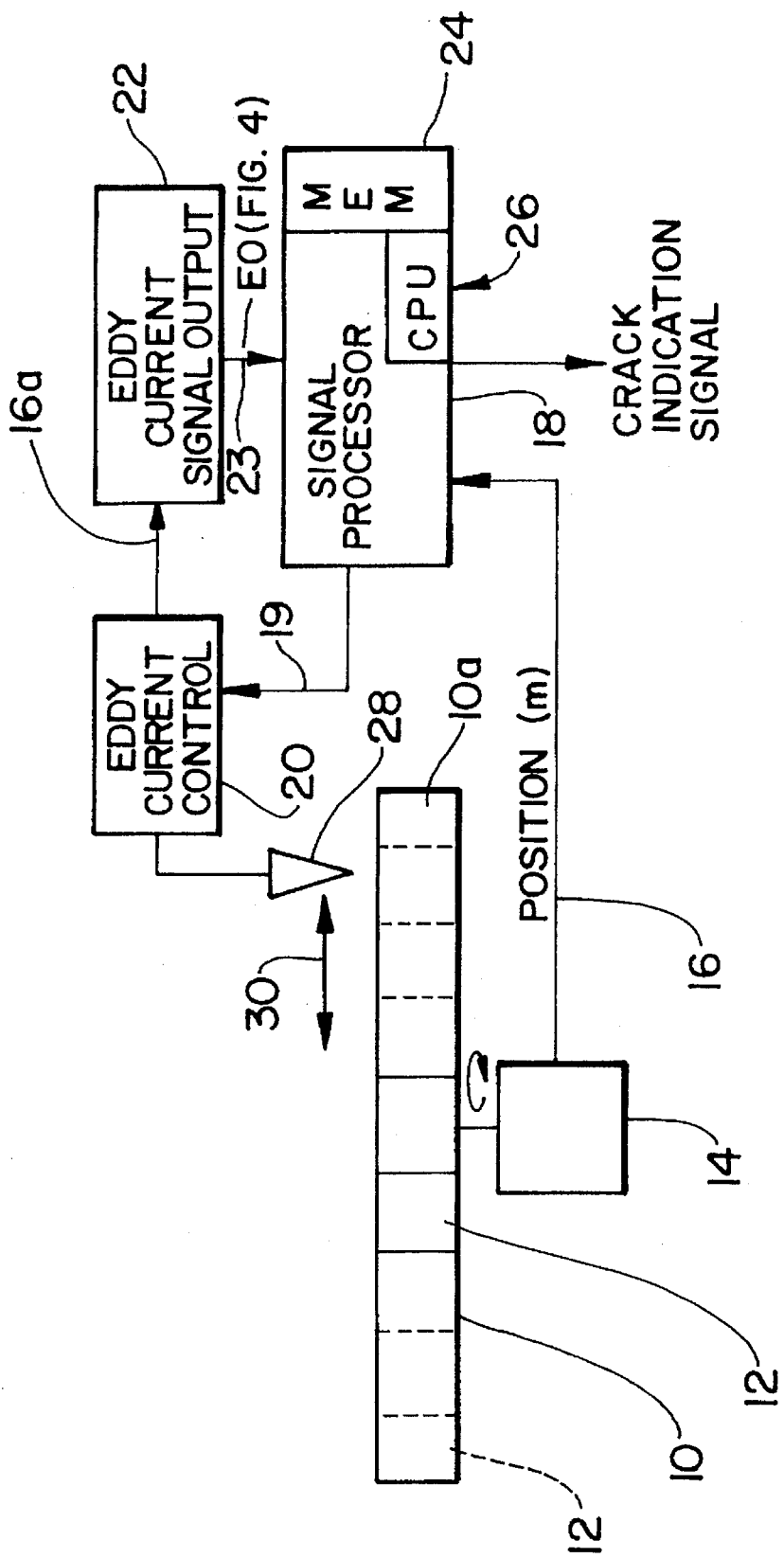
FIG. 1 is a block diagram of a system for detecting cracks using eddy current testing techniques embodying the present invention.
Figure 2:
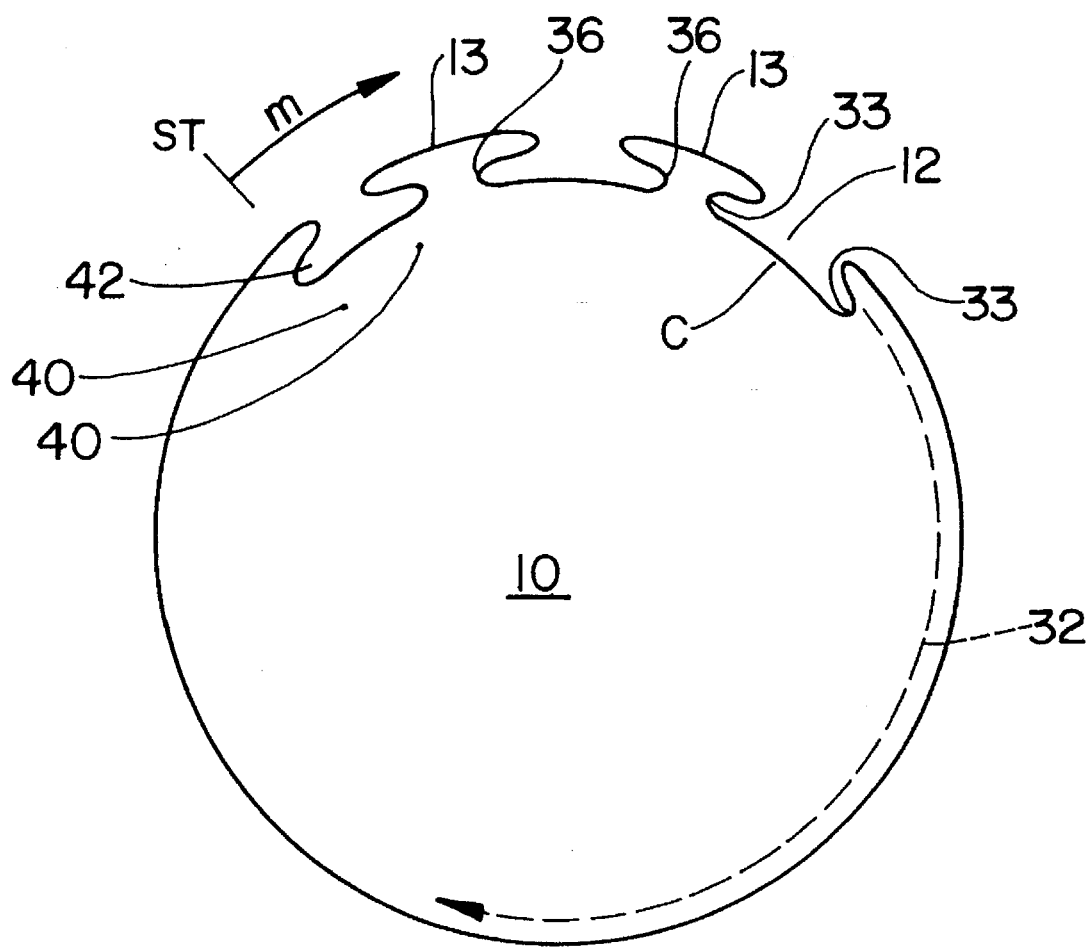
FIG. 2 is plan view of gas turbine disk, showing some of the blade broaches.

In FIG. 1, a circular disk 10, such as a compressor, turbine or fan blade disk found in a gas turbine engine, contains identical blade receiving broaches 12 around its circumference or edge 13, three of these being shown in plan in FIG. 2. On an actual disk the broaches 12 would extend completely around disk. The disk is rotated by a drive 14, which produces a position signal (m) on a line 16, an input to a signal processor 18. The signal processor 18 is connected to an eddy current control 20 and to an eddy current signal output signal processor 22 that produces an eddy current output (EO) electrical signal, shown in FIG. 4, another input to the signal processor 18, in addition to the position signal m. The signal processor 18, which is a programmed computer based device, contains a memory (MEM) 24 for storing programming instructions and other data, and a CPU 26 (central processing unit) for carrying out those instructions. The eddy current control 20 controls the position of an eddy current induction probe and detector 28 that produces signals that are supplied to the eddy current signal processor 18. The probe 28 may be radially positioned (arrow 30), but it should be assumed that it is located to scan the area shown by line 32 in FIG. 2, to detect the characteristics in the curved areas 33 of the broaches 12. For present purposes, it can be assumed that the signal processor 18 provides control signals over the line 19 to cause the eddy current control 20 to operate in known ways (e.g., as described in U.S. Pat. No. 5,130,651, incorporated by reference herein) to control the probe 28 to produce eddy currents in the disk 10 to produce the EO signal. Timing marks 40 (dimples or recesses) identify a starting position on the disk 10.

Figure 4:
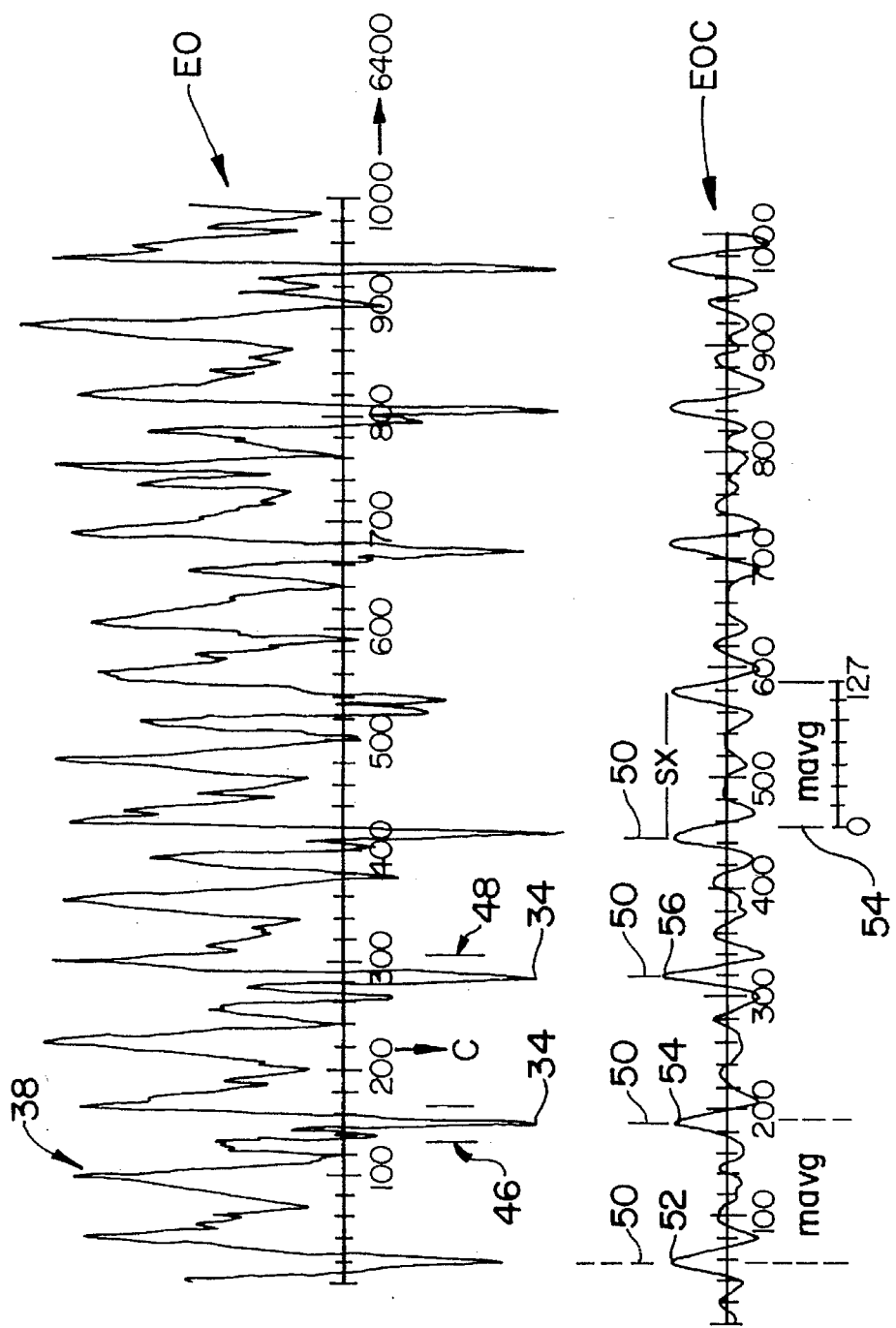
FIGS. 4A, 4B shows two eddy current produced waveforms plotted on a common time base.

Referring to FIG. 4, for convenience there are assumed to be 6400 possible locations (m) in a full disk rotation and the EO signal (data string per m) has value for each location. Generally speaking, the peaks 34 define both sides 36 of a broach 12. The "signature" 38 between the peaks is indicative of the metallic characteristics between those ends. Assuming that the characteristics of each broach are identical (that there are no cracks), the signature would be the same for every broach, except that the timing marks 40 would produce a signature when the broach 36 passes the detector 28.

The non-linear shape of the broaches produces irregular eddy currents, which, in turn, produce the irregular characteristics of the signature or content 38, although the periodic nature of some of that content manifests that the broaches have the same plan shapes, something shown in FIG. 2.

Figure 3:
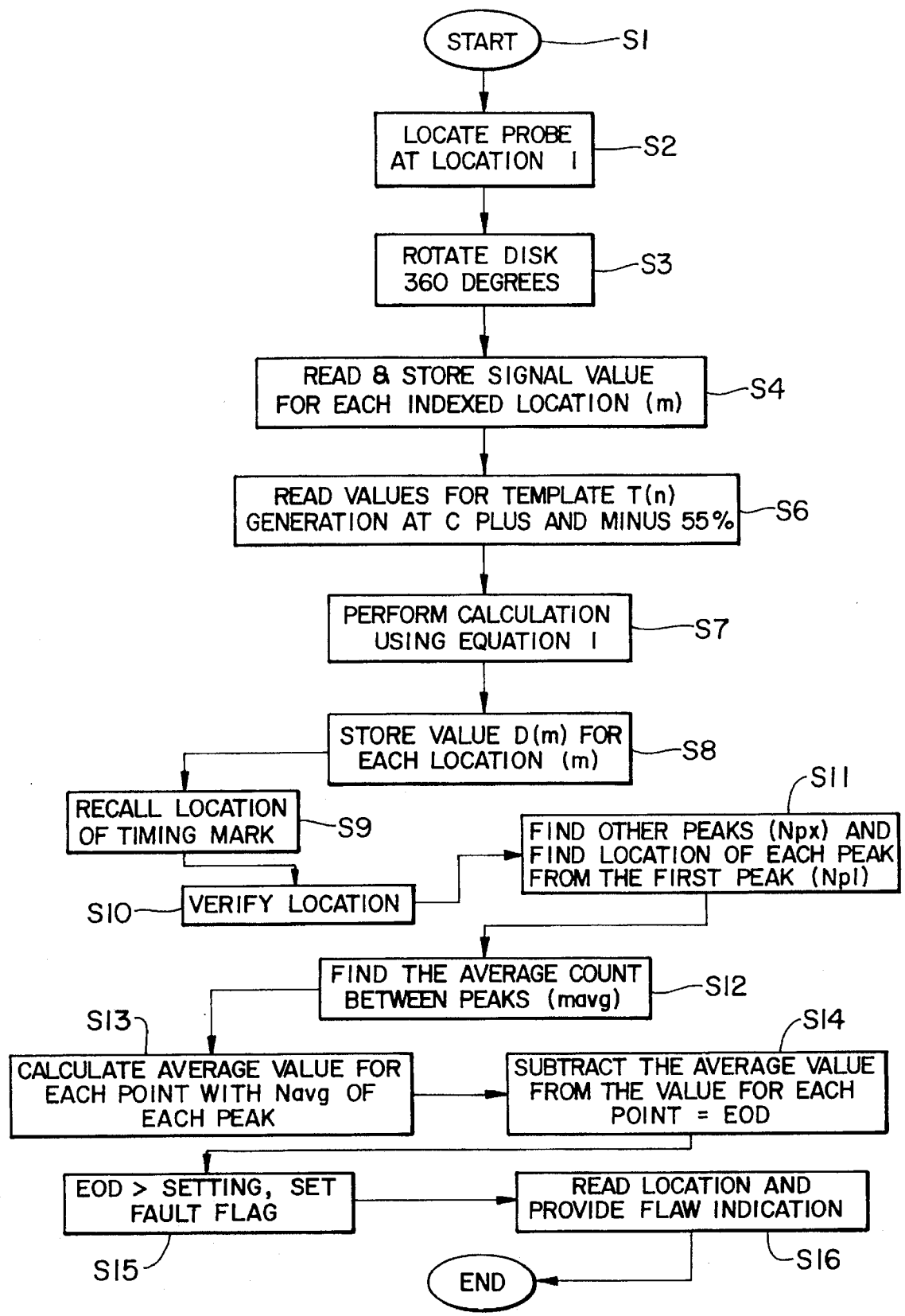
FIG. 3 is a flowchart of signal processing steps embodying the present invention.

The sequences described in FIG. 3 are carried out by the signal processor 18 under the control of the CPU operating according to appropriate program instructions stored in the memory 24. The sequences in FIG. 3 depict an overall process that identifies 1) a crack or flaw at a curved area, such as area 33, from the signature 38 values between peaks 34 (i.e. the beginning and end points 36 of a broach) and 2) the flaw's location in terms of an m position. The process includes the production of a data string, which is stored in the memory, but if shown as a waveform synchronized with the EO signal appears as the "eddy current output-correlated" (EOC) signal in FIG. 4. The process starts at step S1 and moves to step S2 to locate the probe at location 1, above the line 32 in FIG. 2. The disk is rotated 360 degrees in step S3 and the signal value for the EO signal is read and stored for each location m (6400 in FIG. 4) in step S4.

In the next step S6, the location (in units of m) of the center C of a broach 44 is calculated based on the starting location ST. It is desirable that this broach 44 not contain, or be adjacent to, the timing marks (dimples) 40. The length in units of m of any broach 12 is calculated by dividing the total length of m (in this case 6400) by the number of broaches. From this, a template for a typical broach is constructed by reading the values of the EO signal between locations 46 and 48 (bracketing peaks 34), where location 46 is the position C minus 55% of the broach length and location 48 is position C plus 55% of the broach length.

The resulting electronic template comprises a string that is applied, in step S7, to the following correlation equation, where there are n points in the template and m is the number of locations around the complete circumference of the disk.

$$D(m) \text{ correlation} = D(m) \cdot T(1) + D(m+1) \cdot T(2) + D(m+n-1) \cdot T(n) \quad (1)$$

The EOC signal plots the correlation value for each point in the data string D(m) (the EO signal) in relation to each template T(n). The peaks 50 indicate points in the data string where the template lines up the best, i.e., point of highest correlation with the template. Since the template is "around" a broach, the repetition period for points of highest correlation with the template should be one broach period apart. The peaks do not represent the start of the broach, but just the places of best alignment for averaging strings and then subtracting the average. For example, if the template started 50 points (in units of m) before the edge of the broach, the peak of highest correlation would be 50 points (in units of m) prior to the edge of every broach; in other words, not anything to do with the peaks in the EO signal. (It should also be noted that if the template started in the middle of the broach, the peaks in the EOC signal would be in the middle of each broach.) The value D(m) for each location m when correlated to each template location n between 46 and 48 is stored for each location m in step S8, producing a string that would appear as the EOC signal, where the peaks 50 ideally identify the points where the next n points most closely match the template and where the peaks 54, 56 are associated with the adjacent broaches 13.

In step S9, the location of the timing marks 40 is recalled from the memory in order to determine the other locations one period away that do not contain timing marks. Step S10 involves finding a correlation peak in an area that does not contain the timing marks. That this is a valid peak is verified by looking for the next peak of comparable height, e.g., greater than 85% of the peak height. If this is approximately one data period away, the these peaks are the peaks associated with the broaches. If the period is incorrect, the same procedure is initiated with the next highest peak in the EOC signal. The verification process will converge on selecting valid correlation peaks in a short, finite time. The location of the "valid" peaks, approximately one data period apart, are found and stored in step S11. The average count m between those locations is the value "mavg". Thus, the memory contains the EOC signal value for each location m and the average width for each broach. In step S13, the average value for each correlated location is determined. For instance, if the average width is mavg=128, each string SX between valid peaks would have 0–127 values in units of m from a starting location 50. The average value for each location in the strings, e.g. each location 50 is determined. At step S14, the average value for each location in a string SX is subtracted from the actual values for each location m, producing an eddy current output deviation (EOD)signal. Step S15 evaluates the EOD signal either by the process described in U.S. Pat. No. 5,130,651 (incorporated by reference herein) column 7, line 25 to column 8, line 45 (except that compensation of varying lift-off distances is not used) or by setting a FAULT flag if the EOD value (deviation) exceeds a stored setting. The center location of any flaw is indicated in step S16. The process ends at step S17.

With the benefit of the previous discussion of the invention, one of ordinary skill in the may be able to modify an above-described embodiment of the invention, in whole or in part, without departing from the true scope and spirit of the invention.

I claim:

1. An eddy current testing method, characterized by:

assigning location codes to locations along the edge of a metallic part;

producing an eddy current generated signal for each of the locations;

storing first signal values, each having a value of the eddy current generated signal for each location code;

identifying first and second location codes beyond the beginning and end of periodic changes in said first signals;

producing correlation signals from said first and second location codes and other of said location codes, said correlation signals having a magnitude manifesting an extent of correlation between the first signal value for the locations from said first and second location codes and the first signal values of other location codes, said correlation signals being expressed by the function $D(m) \cdot T(1) + D(m+1) \cdot T(2) + D(m+n-1) \cdot T(n)$, where n is a number of locations between said first and second locations. T is the level of said first signal at each of said n locations, m is number of locations along said edge and D is the level of said first signal at each of said m locations;

identifying third and fourth location codes at the beginning and end of each periodic change of maximum correlation in said correlation signals;

producing a width signal with a magnitude manifesting the average increment between said third and fourth location codes, said width signal having n increments;

producing an average first signal value for each of said n increments by determining the average of the first signal value for each of corresponding n increments between said third and fourth location codes; and producing a deviation signal manifesting the difference between said average first signal value and each of said first signal values; and producing a detection signal the magnitude of said detection. Signal being a function of the characteristics of said deviation signal relative to a reference value for said deviation signal.

2. A method according to claim 1, characterized in that:

said first and second location codes bracket the beginning and end of a periodic change in said first signals are determined from the location for the center of a known one of a plurality of recurring features on the part.

3. An eddy current testing device, characterized by:

eddy current probe means for providing an electrical signal from an object;

signal processing means comprising means for storing a first signal manifesting locations along a path of the eddy current probe; for storing second signals, each manifesting the value of said electrical signal provided by said current probe means at each of said locations; for storing a template comprising second signal values associated with one of a plurality of recurring features on the object; for storing third signals that manifest the extent of correlation between the electrical signals produced by said feature and electrical signals for other of said locations associated with other of said recurring features; for providing a fourth signal that represents the average width in increments of said locations with said features, based on electrical signals produced by said feature, for providing a fifth signal that represents the average value of the electrical signals for identical increments, for providing a sixth signal manifesting the deviation between said fifth signal and said second signal exceeds a stored threshold and for providing a detection signal, the magnitude of said detection small being a function of the characteristics of said fifth signal relative to a reference level for said fifth signal, and said third signals being expressed by the function $D(m) \cdot T(1) + D(m+1) \cdot T(2) + D(m+n-1) \cdot T(n)$, where n is a number of locations between said first and second locations; T is the level of said first signal at each of said n locations, m is a number of locations along said edge and D is the level of said first signal at each of said m locations.

4. An eddy current testing device according to claim 3, characterized in that said second signal values comprise electrical signal values for locations that are plus and minus a first percentage measured from the centerline of said one feature.

* * * * *